(12) United States Patent
Rajamani et al.

(10) Patent No.: US 6,469,789 B1
(45) Date of Patent: Oct. 22, 2002

(54) ON-LINE COLOR MEASUREMENT SYSTEM FOR COOLED PRODUCT

(75) Inventors: Ravi Rajamani, Schenectady, NY (US); Vijay Kumar Mallikarjun Hanagandi, Evansville, IN (US)

(73) Assignee: General Electric Company, Niskayuna, NY (US)

( * ) Notice: Subject to any disclaimer, the term of this patent is extended or adjusted under 35 U.S.C. 154(b) by 147 days.

(21) Appl. No.: 09/643,245

(22) Filed: Aug. 22, 2000

(51) Int. Cl.$^7$ .................................................. G01J 3/50
(52) U.S. Cl. ........................ 356/402; 250/226; 356/425
(58) Field of Search ................................. 356/402, 405, 356/406, 407, 425; 250/226

(56) References Cited

U.S. PATENT DOCUMENTS

| | | |
|---|---|---|
| 4,684,488 A | 8/1987 | Rudolph |
| 5,559,173 A | 9/1996 | Campo et al. ............... 523/303 |
| 5,568,266 A | 10/1996 | Ciza et al. ................... 356/402 |
| 5,859,708 A | 1/1999 | Feldman ..................... 356/406 |
| 5,953,129 A | 9/1999 | Anderlik et al. ............ 356/402 |

FOREIGN PATENT DOCUMENTS

EP          0 407 927 A          1/1991

*Primary Examiner*—F. L. Evans
(74) *Attorney, Agent, or Firm*—John F. Thompson; Jill M. Breedlove

(57) ABSTRACT

An on-line color sensor supplies light to a spectrophotometer for color measurement of product after cooling. The product is extruded in a main extruder having a bypass section. The on-line color sensor includes an housing having an interior portion. The housing is positioned proximate to the bypass section and is used to direct the product from the bypass section into the interior portion. A receptacle that is connected to the housing is positioned in the interior portion of the housing to hold the product directed into the interior portion. The product is allowed to cool while being held on the receptacle. A light source is connected to the housing and supplies light to the interior portion of the housing. A light receiver is connected to the housing to capture the light from the light source in the interior portion that is affected by the cooled product. The captured light is supplied to the spectrophotometer to measuring the color of the cooled product in the interior portion of the housing.

42 Claims, 3 Drawing Sheets

ON-LINE COLOR MEASUREMENT SYSTEM FOR COOLED PRODUCT

BACKGROUND OF THE INVENTION

The invention relates to a color measurement system and more particularly to a color measurement system for color measurement of cooled product after the product has been extruded by an extrusion mechanism.

In the manufacturing of some materials, for example, polymeric materials, the product undergoes several manufacturing processes before the final product is created. These processes can be performed in one processing area or at several processing areas. In either case, the product is transported from process to process, or the product is transported to a finishing area. In addition, at the final processing area the product can be formed into various shapes and sizes. Typically, the movement and final forming of the product is accomplished by extruding the material through a conduit. Heating the product so that the product flows similar to a liquid facilitates the extrusion of the product through the conduit.

Many processes, especially the finishing process and forming, desire to identify or measure the color of the cooled product. Color identification and measurement is desired for, among other things, determining the state of the process, determining the quality of the product and sorting the product. However, the heated product can have a different color than the cooled product. In one example, color of the product is identified and measured by directing a sample of the product to a bypass section in the conduit or main extruder. The sample of the product that is directed through the bypass section is collected by an operator and is allowed to cool. The operator manually supplies the portion of the cooled sampled product to a spectrophotometer where the color is measured. This process of color measurement and identification is time consuming and, therefore, increases the manufacturing time of the product which in turn increase the costs associated with manufacturing.

Therefore, there is a desire for an optical color sensor that provides in situ color measurement of a cooled product that automatically takes a sample of the product, expedites sample cool time and provides information relating to the product for analysis.

BRIEF SUMMARY OF THE INVENTION

In one exemplary embodiment, an on-line color sensor is provided for supplying light to a spectrophotometer that measures the color of cooled product. The product is extruded from a main extruder having a bypass section. The on-line color sensor comprises a housing having a top portion proximate to the bypass section and having an open bottom. The housing, the top portion and the open bottom define an internal portion. A funnel is positioned in the top portion and directs product from the bypass section into the interior portion of the housing. A cover hinge is connected to a top cover, a bottom cover and the housing. The cover hinge is used when the top and bottom cover are moved to at least a first position where the top cover covers the top portion and the funnel and where the bottom cover encloses the open bottom of the housing. A receptacle is connected to the housing and positioned in the interior portion proximate to the funnel portion. The receptacle holds the product received from the bypass section, and the product is allowed to cool while being held by the receptacle. A light source is connected to the top cover and provides light through the funnel into the interior portion of the housing. A light receiver is connected to the top cover, or the bottom cover, and the spectrophotometer. The light receiver captures light from the light source in the interior portion that is affected by the cooled product being held on the receptacle. The captured light is supplied to the spectrophotometer and is used to measure the color of the cooled product in the interior portion of the housing.

DETAILED DESCRIPTION OF THE INVENTION

Figure 1:
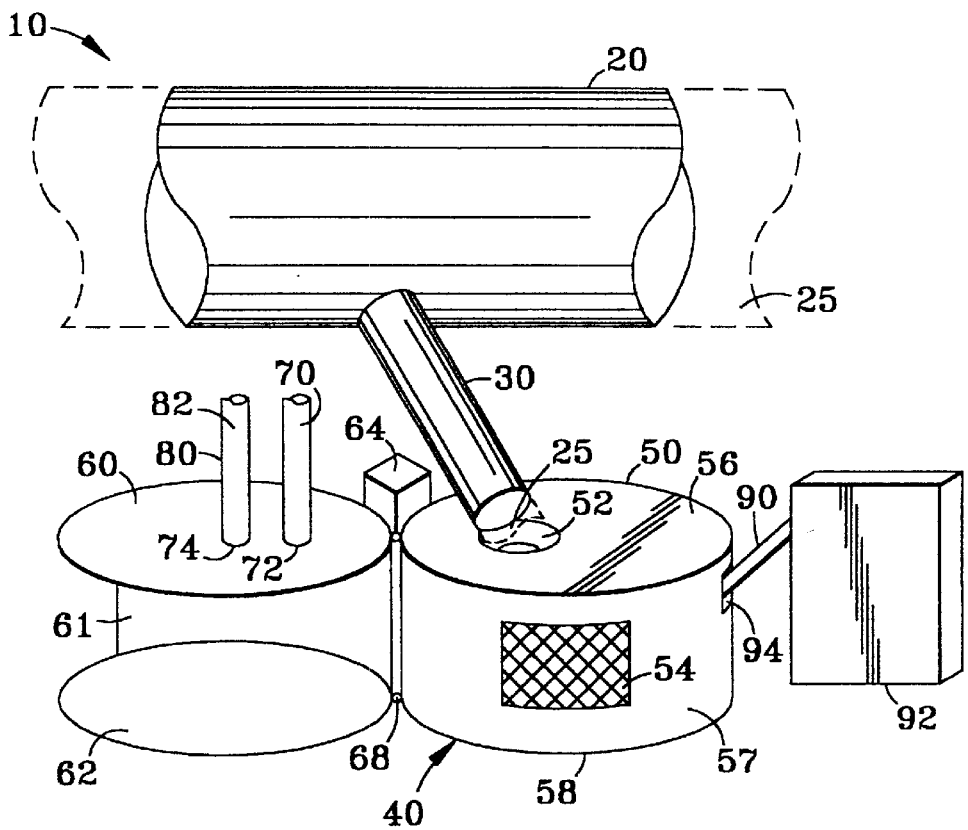
FIG. 1 is a perspective view of one exemplary embodiment of an on-line color measurement system.
Figure 2:
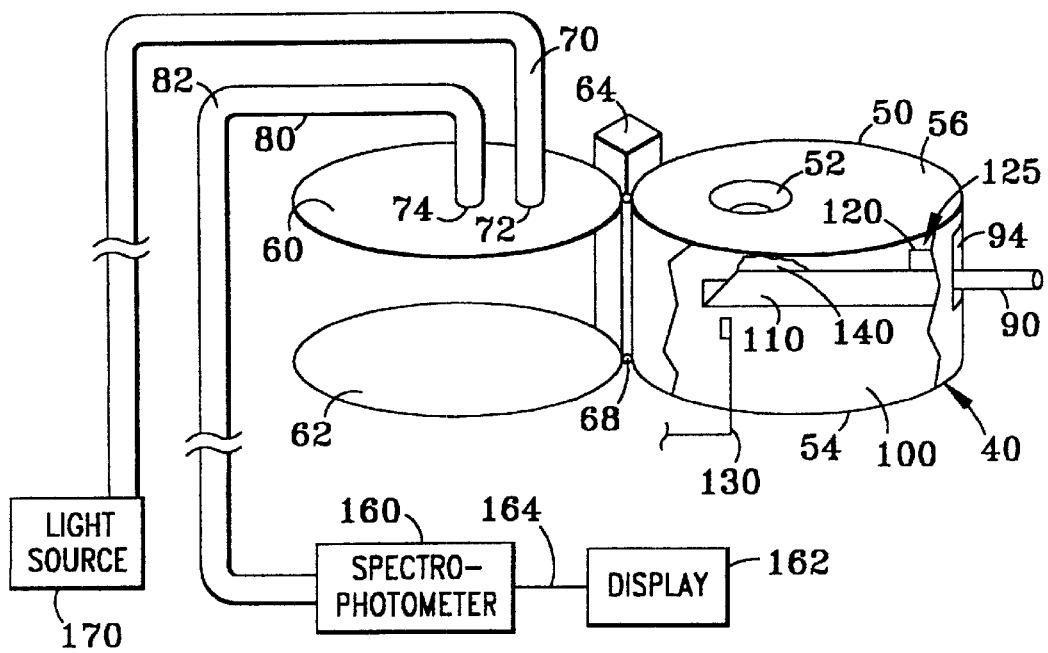
FIG. 2 is a perspective/schematic view of one exemplary embodiment of an on-line color sensor.

As shown in FIG. 1, the manufacturing of certain materials, for example, plastics and polymeric materials, into a product 25 involves a main extruder 20 through which the product 25 is extruded. In one embodiment, the extrusion of the product 25 is provided to move the product 25 from one location to another. In another embodiment, the extrusion of the product 25 is used to form the product 25 into desired shapes and sizes as part of a final or finishing process step. Various manufacturing processes desire to use the color of the product 25 after the product 25 has cooled to assist in manufacturing, fabricating and/or sorting. Typically, the product 25 is heated to facilitate extrusion through the main extruder 20. The heated product 25 depending upon the material properties can have a different color than the cooled product 140 (FIG. 2). Therefore, the color of the heated product 25 may not provide an accurate measurement of the color of the cooled product 140 (FIG. 2). Therefore, in one exemplary embodiment of the present invention, a color measurement system 10 is used to facilitate cooling the heated product 25 and to determine the color of the cooled product 140 (FIG. 2) without requiring an operator to manually determine the color.

Figure 3:
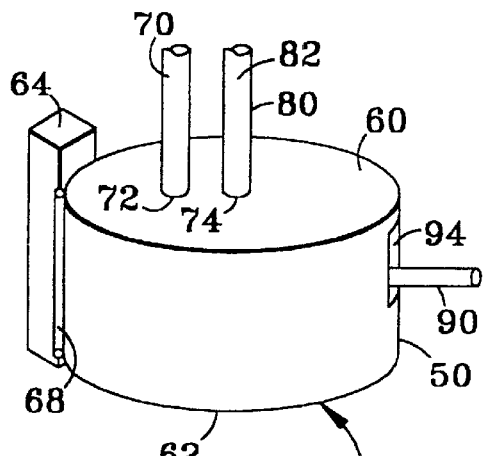
FIG. 3 is a perspective view of another exemplary embodiment of an on-line color sensor.
Figure 4:
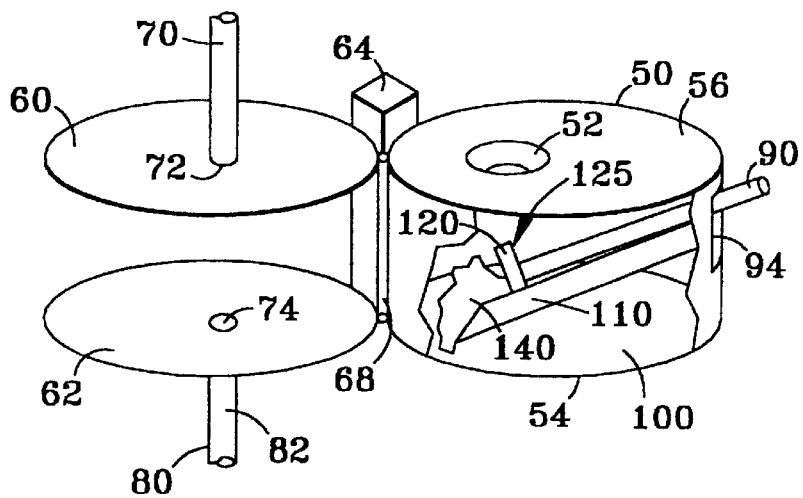
FIG. 4 is a perspective view of yet another exemplary embodiment of an on-line color sensor.

In one embodiment as shown in FIG. 1, a bypass section 30 is connected to the main extruder 20 of the color measurement system 10. An on-line color sensor 40 is positioned proximate to the bypass section 30. The on-line color sensor 40 includes a sensor housing 50. In another embodiment, the sensor housing 50 includes a top portion 56, a side portion 57 and a bottom portion 58 that define an interior potion 100 (FIG. 2). A funnel 52 is located in the top portion 56 of the sensor housing 50. A housing opening 94 is provided in the side portion 57 of the sensor housing 50. A push rod 90 of surface preparation and cleaning mechanism 125 (FIG. 2) extends from the housing opening 94 and connects to a preparation/cleaning actuator 92 that moves at least the surface preparation and cleaning mechanism 125. A fan 54 is located in the side portion 57 of the sensor housing 50. A cover hinge 68 is connected to the sensor housing 50. A top cover 60 and a bottom cover 62 are connected to the cover hinge 68. A cover side portion 61 also connects the top cover 60 and bottom cover 62. A cover actuator 64 is connected to at least the top cover 60 and the bottom cover 62 and is used to move the top cover 60 and the bottom cover 62 from at least a first position (FIG. 3) to a second position (FIGS. 1, 2 and 4).

In one embodiment, a first receptacle 72 and a second receptacle 74 are provided on the top cover 60. As shown in FIG. 2, the first receptacle 72 is connected to a light source 170 via fiber optic bundle 70. The second receptacle 74 comprises a light receiver 80 that is connected via fiber optic bundle 82 to a spectrophotometer 160. A display 162 is connected to the spectrophotometer 160 via connection 164. In one embodiment as shown in FIG. 3, the first receptacle 72 and the second receptacle 74 are positioned such that when the top cover 60 is in the first position, and the fiber optic bundles 70 and 82 optically view into the interior portion 100 through the funnel 52.

As disclosed above, a portion of the product 25 that flow through the main extruder 20 is directed to flow through the bypass section 30, and the on-line color sensor 40 is positioned proximate to the bypass section 30 of the main extruder 20. In a preferred embodiment, the main extruder 20 comprises a viscometer extruder. The bypass section 30 is positioned such that any portion of the product 25 that is extruded from the bypass section 30 is directed into the funnel 52 which then directs the product 25 into the interior portion 100 of the sensor housing 50. In another embodiment, the main extruder 20 or the bypass section 30 include a valve or other mechanism (not shown) that is activated to select when the portion of the product 25 flows through the bypass section 30.

Figure 5:
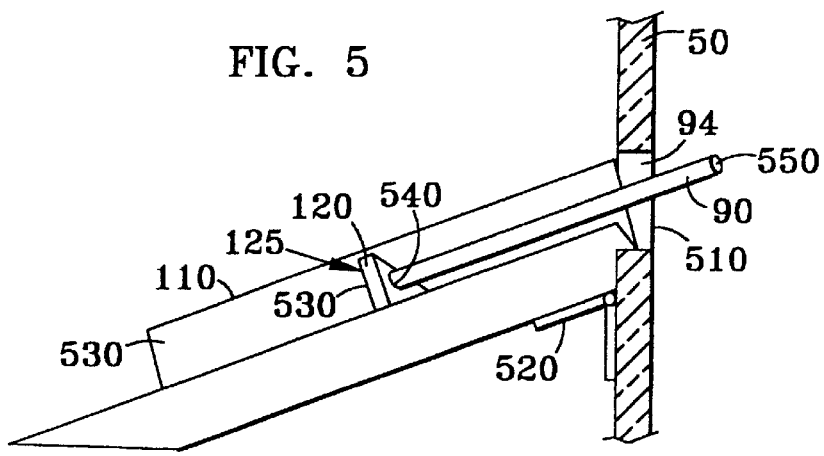
FIG. 5 is a perspective/cross-sectional view of one embodiment of a receptacle for use in an on-line color sensor.

In FIG. 2, the top cover 60 and the bottom cover 62 are shown in the first position where the product 25 (FIG. 1) can flow via the funnel 52 into the interior portion 100 of the sensor housing 50. A receptacle 110 is positioned in the interior portion 100 and is also positioned proximate to the funnel 52 such that product 25 flowing through the funnel 52 is held and/or captured by the receptacle 110. As shown in FIG. 5, in one embodiment, the receptacle 110 is connected to the sensor housing 50 via a hinge 520. In a preferred embodiment, the receptacle 110 comprises a V-groove shape. Once the product 25 is held on the receptacle 110, the surface of the product 25 is prepared for measurement, and it is preferably allowed to cool and become cooled product 140. The fan 54 (FIG. 1) to assist in the cooling of the product 25 provides an airflow in the interior portion 100. A temperature sensor 130 can be provided in the interior portion 100 to monitor the temperature of the product 25 and/or the cooled product 140. The temperature sensor 130 can be connected to a computing or control device (not shown) such that the color of the cooled product 140 is measured only after the cooled product 140 reaches a predetermined temperature.

In a preferred embodiment to assist in the measurement of the color of the cooled product 140, the sensor housing 50 of the on-line color sensor 40 is opaque. In one embodiment, the sensor housing 50 comprises an opaque coating, such as, for example, a deposited coating and/or a painted coating. In another embodiment, the sensor housing 50 comprises an opaque casing, such as, for example, a metal or plastic housing. The opaque characteristic of the sensor housing 50 ensures that exterior light cannot enter the interior portion 100 and/or light from the light source 170 is not dissipated from the interior portion 100. In addition, the sensor housing 50 also includes a covering 510 in the housing opening 94 of the sensor housing 50. The covering 510 also ensures that a minimal amount of exterior light enters the interior portion 100 of the sensor housing through the housing opening 94 when the push rod 90 extends therefrom. It should be appreciated that the side portion 61, shown in FIG. 1, is one embodiment used to cover the fan 54 when the top cover 60 and the bottom cover 62 are moved to the first position to prevent light from entering the interior portion.

As shown in FIGS. 1 and 2, the on-line color sensor 40 includes a first receptacle 72 and a second receptacle 74. In one embodiment, the first receptacle 72 and the second receptacle 74 are located in the top cover 60 and operate through the funnel 52 to provide and receive light from the interior portion 100 of the sensor housing 50. In another embodiment, as shown in FIG. 4, the second receptacle 74 is positioned in the bottom cover 62 to receive transmitted light from the fiber optic bundle 70 positioned at the first receptacle 72 in the top cover 60. The configuration of the first receptacle 72 and the second receptacle 74 shown in FIG. 4 allows the on-line color sensor 40 to measure the color of products 25 that are transparent and/or translucent. When the product 25 is translucent and/or transparent, light passes through the product 25. Therefore, in one embodiment, the first receptacle 72 and the second receptacle 74 are positioned in the top cover 60 and the bottom cover 62, as shown in FIG. 4. In this configuration, the light from the fiber optic bundle 82 that passes through the product 25 also passes through the receptacle 110 and is collected by the light receiver 80. The collected light is provided to the spectrophotometer 160 for color measurement.

Figure 8:
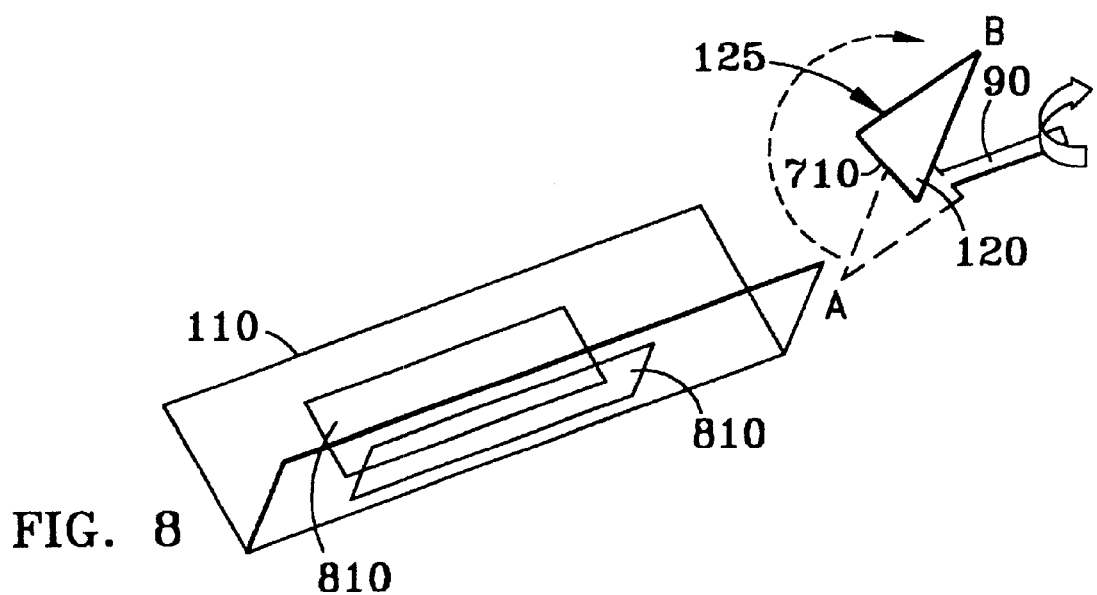
FIG. 8 is a perspective view of yet another embodiment of a preparation/cleaning mechanism illustrating a transformation from a cleaning configuration to sample preparation configuration.

In embodiments where the product 25 is transparent and/or translucent, the receptacle 110 can be composed of a translucent and/or transparent material, such as for example quartz. In other embodiments where the product 25 is transparent and/or translucent, the receptacle 110 can comprises a transparent and/or translucent window 810 (FIG. 8). In a preferred embodiment, the window 810 is composed of quartz. In these embodiments, light from the fiber optic bundle 82 can pass through the receptacle 110. It should be appreciated that in the embodiments where the product 25 is translucent and/or transparent, the spectrophotometer 160 (FIG. 2) can be calibrated to determine any color influence that the receptacle 110 contributes to the color measurement. It should also be appreciated that in other embodiments the first receptacle 72 and the second receptacle 74 can be placed in other positions wherein light is provided into the interior portion 100, and the light that is received is affected by the cooled product 140.

The first receptacle 72 is connected to the light source 170 via a fiber optic bundle 70 that comprises, in one embodiment, a plurality of optical fibers housed in an opaque casing. In one embodiment, the light source 170 comprises a calibrated light source such that the light that is supplied to the on-line color sensor 40 can be precisely controlled. In another embodiment, the light source 170 comprises a white light source. The light receiver 80 can, in one embodiment, comprise the fiber optic bundle 82 that is connected to the spectrophotometer 160. In addition in one embodiment, the fiber optic bundle 82 comprises a plurality of optical fibers housed in an opaque casing. It should be appreciated that the light receiver 80 can comprise any mechanism that collects and/or transmits the light from the on-line color sensor 40 to the spectrophotometer 170. It should also be appreciated that the fiber optic bundles 70 and 82 can comprise a device that transmits or conducts light from one source to another, and the fiber optic bundles 70 and 82 should not be limited to only those disclosed herein.

The spectrophotometer 160 includes electronics that are used to determine the color from the light that is received by the light receiver 80. The spectrophotometer 160 is connected to a display 162 via connection 164. In one embodiment, the display 162 provides information and/or data relating to the color of the cooled product 140. This information can be used by an operator or a control device (not shown) to control the manufacturing process of the cooled product 140. It should be appreciated that the spectrophotometer 160 can be connected to a control device (not shown) such as a microprocessor and supplies control signals or data relating to the color of the cooled product 140 for controlling the manufacturing of the product 25. In addition, the spectrophotometer 160 may be housed in or connected to a computing device (not shown) that manipulates the light, data and/or information supplied the on-line color sensor 40.

The light supplied to the on-line color sensor 40 is used to measure the color of the cooled product 140. In one embodiment, the cooled product 140 is opaque or semitransparent and has very low light transmission properties. As such, in this embodiment, the material properties of the cooled product 140 allow very little or even no light to pass through the cooled product 140. Therefore, the portion of the cooled product 140 that is held on the receptacle 110 reflects light from the light source 170. For this material type, in one embodiment, the first receptacle 72 and the second receptacle 74 can be positioned in the top cover 60 and positioned over the funnel 52 when the top cover 60 is in the first position, as shown in FIG. 3. Thus in this configuration, the light receiver 80 collects light supplied by the light source 170 that is reflected by the cooled product 140, and the light receiver 80 supplies this light to the spectrophotometer 160. However, in other embodiments, the material properties of the cooled product 140 allow light to be transmitted through and/or pass through the cooled product 140. In these embodiments, the first receptacle 72 and the second receptacle 74 can be positioned at other locations such as, for example, in the top cover 60, in the bottom cover 62 (as shown in FIG. 4. In addition, it should be appreciated that the first receptacle 72 and the second receptacle 74 can also be positioned in the sensor housing 50, in the interior portion 100, in the receptacle 110 or in the surface preparation and cleaning mechanism 125. Similarly, in this embodiment, the light source 170 supplies light to the on-line color sensor 40 that passes through the cooled product 140. The light receiver 80 collects light that is transmitted through the cooled product 140 and supplies that light to the spectrophotometer 1600. It should be appreciated that the light from the light source 170 may be affected by the cooled product 140 in other ways other than reflection of and transmission through the cooled product 140, and the present invention should not be limited to the embodiments disclosed herein.

The color measurement system 10 and on-line color sensor 40, as shown in FIGS. 1–4, measure the color of the cooled product 140 that is positioned in the interior portion 100 of the on-line color sensor 40. In one embodiment, the product 25 flows through the funnel 52 of the on-line color sensor 40 and into the interior portion 100 of the sensor housing 50. The product 25 is held and/or captured in the interior portion 100 by the receptacle 110. In one embodiment, as shown in FIG. 2, the receptacle 110 holds the product 25 and/or cooled product 140 while the receptacle 110 is perpendicular to the sensor housing 50 to facilitate holding or capturing of the product 25 and/or cooled product 140. In one embodiment, the main extruder 20 or the bypass section 30 contains a valve (not shown) that is used to control the amount of the product 25 that flow into the interior portion 100. In another embodiment, the length of time that the product 25 flows into the interior portion 100 is measured, and after a predetermined time, the top cover 60 is moved by the cover actuator to the first position, as shown in FIG. 3. In a preferred embodiment, the cover actuator 64 comprises an electric motor. In the first position, the top cover 60 covers the funnel 52 and the top portion 56, and the product 25 is prevented from flowing into the funnel 52. It should be appreciated that the cover actuator 64 can move the top cover 60 and the bottom cover 62 together or individually.

Figure 6:
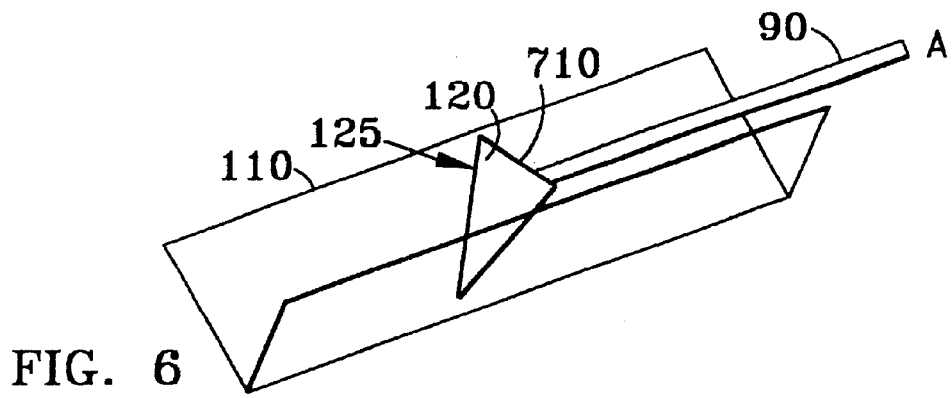
FIG. 6 is a perspective view of one embodiment of a preparation/cleaning mechanism in a cleaning configuration.
Figure 7:
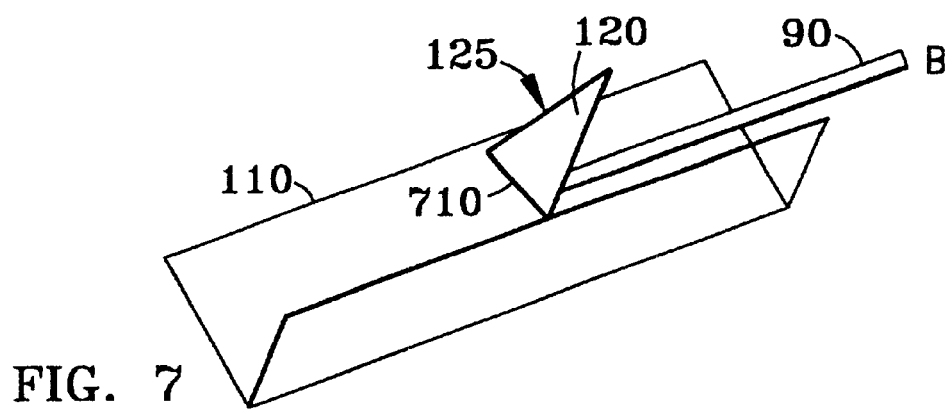
FIG. 7 is a perspective view of another embodiment of a preparation/cleaning mechanism in a sample preparation configuration.

Once the desired amount of product 25 is held or captured by the receptacle 110, the surface of the product is prepared for the color measurement. The preparation of the surface of the product 25 involves passing a knife-edge 710 (FIG. 7) over the surface of the product 25 positioned on the receptacle 110 to remove excess product 25 and to produce a substantially flat surface on the sample of the product 25. In one embodiment, the knife-edge 710 is included as part of the push rod face 120 in the surface preparation and cleaning mechanism 125, as shown in FIGS. 6–8. To use the knife-edge 710, the preparation/cleaning actuator 92, as shown in FIG. 8, rotates the push rod 90. Specifically by rotating the push rod 90, the push rod face 120 can be moved from position A (FIG. 6) to position B (FIG. 7) and vise versa. Position B (FIG. 7) allows the knife-edge 710 to contact the sample of the product 25 to produce a substantially flat surface. In a preferred embodiment, as shown in FIGS. 6–8, the push rod face 120 is positioned on the push rod 90 at an angle other than 90° to facilitate the cleaning and the sample preparation of the product 25.

The flat surface produced by the knife-edge 710 aids in the color measurement by making a reflective surface for products 25 that are opaque and a substantially even surface for the transmission of light for products 25 that are transparent and/or translucent. The preparation of the sample of product 25 makes the light reflected from or transmitted through the product 25 consistent between various products 25. In addition, the surface preparation of the product aids in the calibration of the color measurement system 10 by making the reflected or transmitted light uniform. It should be appreciated that the preparation of the sample surface is provided in one embodiment of the color measurement system 10 and other embodiments need not necessarily include this feature.

Once the surface is prepared in the hot, or molten state, the product 25 is allowed to cool and to form a cooled product 140. In another embodiment, the fan 54 can be used to facilitate the cooling of the product 25. When the product 25 is cooled to form the cooled product 140, the color of the cooled product 140 is measured. To measure the color of the cooled product 140, the color measurement system 10 provides light into the on-line color sensor 40 from the light source 170. The light from the light source 170 is provided through the fiber optic bundle 70 to the interior portion 100. The cooled product 140 in the interior portion 100 of the on-line color sensor 40 affects the light transmitted to the on-line color sensor 40. As mentioned previously, the material properties of the cooled product 140 affect the light by, for example, reflecting the light from the cooled product 140 and/or allowing the light to be transmitted through the cooled product 140. The light receiver 80 receives the light affected by the cooled product 140 in the on-line color sensor 40. The light that is collected by the light receiver 80 is transmitted to a spectrophotometer 160 that analyzes the light to determine the color of the cooled product 140. Information and/or data relating to the color is transmitted to a display 162 or a computing device (not shown). The information and/or data relating to the color of the cooled product 140 can be used to control the manufacturing of the product 25.

As shown in FIGS. 5 and 6, once the color measurement has taken place, the push rod 90 is rotated so that the push rod face 120 is positioned in the receptacle 110, and the surface preparation and cleaning mechanism 125 removes the cooled product 140 from the receptacle 110. The push rod 90 includes a first distal end 540 connected to the push rod face 120 and a second distal end 550 connected to the preparation/cleaning actuator 92. In a preferred embodiment, the push rod face 120 comprises a triangular shape that fits in a preferred embodiment of the receptacle 110 comprising a V-groove shape. To clean the product 25 from the receptacle 110, the push rod face 120 is rotated to position A (FIG. 6). Once the push rod face 120 is in position A (FIG. 6), the preparation/cleaning actuator 92 exerts a linear force on the push rod 90 such that the push rod face 120 contacts the product 25 to push the product 25 from the receptacle 110.

In one embodiment, as shown in FIG. 5–8, the receptacle 110 can be angled using hinge 520 to facilitate removal of the cooled product 140. In another embodiment, the preparation/cleaning actuator 92 moves the receptacle 110 to the desired angle. In another embodiment, the preparation/cleaning actuator 92 comprises an electric motor. In even another embodiment, the surfaces that contact the product 25 and/or cooled product 140 have a surface coating 530, such as Teflon, that assists in removal of the product 25 and/or cooled product 140. In a preferred embodiment, the bottom portion 58 is open. Therefore, when the top cover 60 and the bottom cover 62 are moved from the first position (FIG. 3) and the cooled product 140 is pushed from the receptacle 110, the cooled product 140 drops out the open bottom 54 of the sensor housing 50 for disposal.

The foregoing discussion of the invention has been presented for purposes of illustration and description. Further, the description is not intended to limit the invention to the form disclosed herein. Consequently, variations and modifications commensurate with the above teachings, and with the skill and knowledge of the relevant art, are within the scope of the present invention. The embodiment described herein above is further intended to explain the best mode presently known of practicing the invention and to enable others skilled in the art to utilize the invention as such, or in other embodiments, and with the various modifications required by their particular application or uses of the invention. It is intended that the appended claims be construed to include alternative embodiments to the extent permitted by the prior art.

What is claimed is:

1. An on-line color sensor supplying light to a spectrophotometer for color measurement of product after cooling, the product being extruded from a main extruder having a bypass section, the on-line color sensor comprising:

a housing having a top portion proximate to the bypass section and having an open bottom wherein the housing, the top portion and the open bottom define an internal portion;

a funnel positioned in the top portion for directing product from the bypass section into the interior portion of the housing;

a cover hinge connected to a top cover, a bottom cover and the housing, the cover hinge allowing the top and bottom cover to move to at least a first position wherein the top cover covers the top portion and the funnel and wherein the bottom cover encloses the open bottom of the housing;

a receptacle connected to the housing and positioned in the interior portion proximate to the funnel portion, the receptacle holding the product received from the bypass section wherein the product cools while being held by the receptacle;

a light source connected to the top cover for providing light through the funnel into the interior portion of the housing;

a light receiver connect to the top cover and the spectrophotometer, the light receiver for capturing light from the light source in the interior portion that is affected by the cooled product held on the receptacle, the captured light being supplied to the spectrophotometer for measuring the color of the cooled product in the interior portion of the housing.

2. The on-line color sensor of claim 1 further comprising a cleaning mechanism contacting on the receptacle for removing product from the receptacle.

3. The on-line color sensor of claim 2 wherein the cleaning mechanism comprises:

a push rod having a first distal end and a second distal end, the first distal end extending outside of the housing; and a face connected to the second distal end for contacting and moving along the receptacle for removing product from the receptacle.

4. The on-line color sensor of claim 3 wherein the face further comprises a knife-edge for contacting the product to form a substantially flat surface on the product.

5. The on-line color sensor of claim 3 wherein the cleaning mechanism further comprises a non-stick, non-reactive coating on a portion of the face contacting the product.

6. The on-line color sensor of claim 3 wherein the cleaning mechanism further comprises an actuator connected to the first distal end of the push rod for moving the push rod and the receptacle.

7. The on-line color sensor of claim 6 wherein the actuator rotates the push rod moving the face from a first position to a second position.

8. The on-line color sensor of claim 1 wherein the receptacle is hinged to the housing.

9. The on-line/color sensor of claim 1 wherein the light source comprises a calibrated light source.

10. The on-line color sensor of claim 1 wherein the light source comprises a white light source.

11. The on-line color sensor of claim 1 wherein the spectrophotometer is connected to a display.

12. The on-line color sensor of claim 11 wherein the display presents data related to the color of the cooled product.

13. The on-line color sensor of claim 1 wherein the receptacle comprises a V-groove shape.

14. The on-line color sensor of claim 1 wherein each of the receptacle and funnel further comprise a non-stick, non-reactive coating on a surface that contacts the product.

15. The on-line color sensor of claim 1 further comprising a fan connected to the housing for cooling the product in the interior portion of the housing.

16. The on-line color sensor of claim 1 further comprising an actuator connected to and for moving the top cover and bottom cover.

17. The on-line color sensor of claim 1 further comprising a temperature sensor for measuring a temperature of the product positioned in the interior portion of the housing and a control device connected to the temperature sensor for monitoring and controlling the temperature of the product.

18. The on-line color sensor of claim 1 wherein each of the housing, the top cover and the bottom cover are composed of a metallic material.

19. The on-line color sensor of claim 1 wherein the housing is opaque.

20. An on-line color sensor for supplying light to a spectrophotometer for color measurement of product after cooling, the product being extruded in a main extruder having a bypass section, the on-line color sensor comprising:
 a housing having an interior portion, the housing positioned proximate to the bypass section and directing product from the bypass section into the interior portion;
 a receptacle connected to the housing and positioned in the interior portion of the housing for holding the product being directed into the interior portion wherein the product cools while being held on the receptacle;
 a light source connected to the housing for supplying light to the interior portion of the housing;
 a light receiver connected to the housing for capturing light from the light source in the interior portion that is affected by the cooled product, the captured light being supplied to the spectrophotometer for measuring the color of the cooled product in the interior portion of the housing.

21. The on-line color sensor of claim 20 further comprising a cleaning mechanism contacting the receptacle for removing product from the receptacle.

22. The on-line color sensor of claim 20 further comprising a fan connected to the housing for cooling the product in the interior portion of the housing.

23. The on-line color sensor of claim 20 wherein the light source comprises a calibrated light source.

24. The on-line color sensor of claim 20 wherein the light source comprises a white light source.

25. The on-line color sensor of claim 20 wherein the spectrophotometer is connected to a display for displaying information relating to the color of the product.

26. The on-line color sensor of claim 20 wherein the housing is opaque.

27. The on-line color sensor of claim 20 wherein the receptacle is composed of a material allowing light from the light source to pass through the receptacle.

28. The on-line color sensor of claim 20 wherein the receptacle comprises a window allowing light from the light source to pass through the receptacle via the window.

29. An on-line color sensor supplying light to a spectrophotometer for color measurement of product after cooling, the product being extruded from a main extruder having a bypass section, the on-line color sensor comprising:
 a housing having a top portion proximate to the bypass section and having an open bottom, the housing, the top portion and the open bottom defining an internal portion;
 a funnel positioned in the top portion for directing product from the bypass section into the interior portion of the housing;
 a cover hinge connected to a top cover, a bottom cover and the housing, the cover hinge allowing the top and bottom cover to move to at least a first position wherein the top cover covers the top portion and the funnel and wherein the bottom cover encloses the open bottom of the housing;
 a receptacle connected to the housing and positioned in the interior portion proximate to the funnel portion, the receptacle holding the product received from the bypass section wherein the product cools while being held by the receptacle;
 a light source connected to the top cover for providing light through the funnel into the interior portion of the housing;
 a light receiver connect to the bottom cover and the spectrophotometer, the light receiver for capturing light from the light source in the interior portion that is affected by the cooled product held on the receptacle, the captured light being supplied to the spectrophotometer for measuring the color of the cooled product in the interior portion of the housing.

30. The on-line color sensor of claim 29 further comprising a cleaning mechanism contacting on the receptacle for removing product from the receptacle.

31. The on-line color sensor of claim 30 wherein the cleaning mechanism comprises:
 a push rod having a first distal end and a second distal end, the first distal end extending outside of the housing; and
 a face connected to the second distal end for contacting and moving along the receptacle for removing product from the receptacle.

32. The on-line color sensor of claim 31 wherein the face further comprises a knife-edge for contacting the product to form a substantially flat surface on the product.

33. The on-line color sensor of claim 31 wherein the cleaning mechanism further comprises a non-stick, non-reactive coating on a portion of the face contacting the product.

34. The on-line color sensor of claim 31 wherein the cleaning mechanism further comprises an actuator connected to the first distal end of the push rod for moving the push rod and the receptacle.

35. The on-line color sensor of claim 34 wherein the actuator rotates the push rod moving the face from a first position to a second position.

36. The on-line color sensor of claim 29 wherein the receptacle is hinged to the housing.

37. The on-line color sensor of claim 29 wherein the light source comprises a calibrated light source.

38. The on-line color sensor of claim 29 wherein the light source comprises a white light source.

39. The on-line color sensor of claim 29 wherein the spectrophotometer is connected to a display for displaying information relating to the color of the product.

40. The on-line color sensor of claim 29 wherein the housing is opaque.

41. The on-line color sensor of claim 29 wherein the receptacle is composed of a material allowing light from the light source to pass through the receptacle.

42. The on-line color sensor of claim 29 wherein the receptacle comprises a window allowing light from the light source to pass through the receptacle via the window.

* * * * *